United States Patent
Carrier

(10) Patent No.: US 9,533,080 B1
(45) Date of Patent: Jan. 3, 2017

(54) LAPAROSCOPIC RETRACTOR AND SUCTION DEVICE

(71) Applicant: Vicki J. Carrier, Lantana, FL (US)

(72) Inventor: Vicki J. Carrier, Lantana, FL (US)

( * ) Notice: Subject to any disclaimer, the term of this patent is extended or adjusted under 35 U.S.C. 154(b) by 56 days.

(21) Appl. No.: 14/584,333

(22) Filed: Dec. 29, 2014

Related U.S. Application Data

(60) Provisional application No. 61/945,305, filed on Feb. 27, 2014.

(51) Int. Cl.
  *A61B 1/32* (2006.01)
  *A61M 1/00* (2006.01)
  *A61B 17/02* (2006.01)
  *A61B 17/00* (2006.01)

(52) U.S. Cl.
  CPC ........ *A61M 1/0086* (2014.02); *A61B 17/0218* (2013.01); *A61M 1/0039* (2013.01); *A61B 1/32* (2013.01); *A61B 2017/00353* (2013.01); *A61B 2217/005* (2013.01); *A61M 2205/0216* (2013.01)

(58) Field of Classification Search
  CPC . A61B 17/0218; A61B 1/32; A61B 2217/005; A61B 2017/00353
  See application file for complete search history.

(56) References Cited

U.S. PATENT DOCUMENTS

| | | | |
|---|---|---|---|
| 5,062,847 A | 11/1991 | Barnes | |
| 5,152,279 A | 10/1992 | Wilk | |
| 5,178,133 A | 1/1993 | Pena | |
| 5,267,554 A | 12/1993 | Wilk | |
| 5,271,385 A | 12/1993 | Bailey | |
| 5,273,026 A | 12/1993 | Wilk | |
| 5,307,805 A | 5/1994 | Byrne | |
| 5,318,586 A | 6/1994 | Ereran | |
| 5,439,476 A | 8/1995 | Frantzides | |
| 8,221,316 B2 * | 7/2012 | DeGould | A61B 17/0206 600/205 |
| 9,005,196 B2 * | 4/2015 | Lingeman | A61B 18/22 606/41 |
| 9,095,299 B2 * | 8/2015 | Ray | A61B 1/32 |
| 2013/0046297 A1 * | 2/2013 | Lingeman | A61B 18/22 606/41 |

FOREIGN PATENT DOCUMENTS

IL  WO 2011123274 A1 * 10/2011 ............. A61B 17/22

* cited by examiner

*Primary Examiner* — Ellen C Hammond
(74) *Attorney, Agent, or Firm* — Robert C. Montgomery; Montgomery Patent & Design, LP.

(57) ABSTRACT

A laparoscopic retractor and suction device includes a shaft including a distal end and an opposed proximal end. The shaft defines an internal suction channel extending from the distal end to the proximal end. The device includes a head attached to the distal end of the shaft and in fluid communication with the suction channel. The head is movable from a collapsed configuration to a deployed configuration.

18 Claims, 4 Drawing Sheets

LAPAROSCOPIC RETRACTOR AND SUCTION DEVICE

RELATED APPLICATIONS

The present invention was first described in and claims the benefit of U.S. Provisional Application No. 61/945,305, filed Feb. 27, 2014 the entire disclosures of which are incorporated herein by reference.

FIELD OF THE INVENTION

The present invention relates generally to laparoscopic devices and, more particularly, to a laparoscopic retractor and suction device.

BACKGROUND OF THE INVENTION

There are a wide variety of surgical instruments used in gynecological, thoracic, laparoscopic, robotic, and similar surgeries. Two (2) of the most common instruments are a retractor and a suction device. The retractor is commonly used to hold the bowel out of the surgical field, while the suction device is used to remove pooling blood and fluids via suction.

However, during laparoscopic surgery, these instruments must be used through very small openings in the patient's skin. Currently there is an open ended hard metal suction irrigator that can cause damage to the bowel by retracting with it or suctioning tissue that occludes the open tip. There is also an expandable retractor, but when it is removed to perform suction, exposure is lost.

Accordingly, there exists a need for a means by which the functions of retraction and suction can be performed by a single device, without the disadvantages as described above.

SUMMARY OF THE INVENTION

The inventor has recognized the aforementioned inherent problems and lack in the art and observed that there is a need for laparoscopic retractor and suction device that provides increased functionality and patient health in a manner that is not only quick, easy, effective, and safe. The development of the present invention, which will be described in greater detail herein, substantially departs from conventional solutions to fulfill this need.

In one (1) embodiment, the disclosed laparoscopic retractor and suction device includes a shaft including a distal end and an opposed proximal end. The shaft defines an internal suction channel extending from the distal end to the proximal end. The device includes a head attached to the distal end of the shaft and in fluid communication with the suction channel. The head is movable from a collapsed configuration to a deployed configuration.

In another embodiment, the disclosed laparoscopic retractor and suction device includes a shaft including a distal end and an opposed proximal end. The shaft defines an internal suction channel extending from the distal end to the proximal end. The proximal end of the shaft includes a vacuum adapter configured to connect to a vacuum hose of an aspiration system and fluidly connect the suction chamber to the vacuum hose. The laparoscopic retractor and suction device includes a handle covering a portion of the shaft about the proximal end of the shaft. The vacuum adapter extends beyond the handle. The laparoscopic retractor and suction device includes a head stem receivably connected within the suction channel at the distal end of the shaft. The laparoscopic retractor and suction device includes head tip connected to the head stem. The head stem and the head tip define a central channel extending through the head stem and the head tip and being in fluid communication with the suction channel. The head tip including a plurality of suction capillaries extending from an exterior of the head tip to the central channel and being in fluid communication with the central channel. The laparoscopic retractor and suction device includes a sliding collar movably connected around the shaft. The laparoscopic retractor and suction device includes a first linkage including a first end pivotally connected to the head tip and an opposed second end. The laparoscopic retractor and suction device includes a second linkage including a first end pivotally connected to the head tip and an opposed second end. The first linkage and the second linkage being directly opposite one another relative to the shaft. The laparoscopic retractor and suction device includes a third linkage including a first end pivotally connected to the second end of the first linkage and an opposed second end pivotally connected to the sliding collar. The laparoscopic retractor and suction device includes a fourth linkage including a first end pivotally connected to the second end of the second linkage and an opposed second end pivotally connected to the sliding collar. The third linkage and the fourth linkage being directly opposite one another relative to the shaft. The laparoscopic retractor and suction device includes a slide shaft including a distal end connected to the sliding collar and an opposed proximate end. The laparoscopic retractor and suction device includes a knob connected to the proximate end of the slide shaft. The laparoscopic retractor and suction device includes an expandable cover disposed over the first, second, third, and fourth linkages. Linear movement of the knob linearly moves the slide shaft and the sliding collar along the shaft for moving the first and third linkages and the second and fourth linkages between a collapsed configuration and a deployed configuration. The first and third linkages and the second and fourth linkages move outwardly to expand the cover when in the deployed configuration. The first and third linkages and the second and fourth linkages move inwardly to retract the cover when in the collapsed configuration.

Furthermore, the described features and advantages of the disclosure may be combined in various manners and embodiments as one skilled in the relevant art will recognize. The disclosure can be practiced without one (1) or more of the features and advantages described in a particular embodiment.

Further advantages of the present disclosure will become apparent from a consideration of the drawings and ensuing description.

BRIEF DESCRIPTION OF THE DRAWINGS

The advantages and features of the present disclosure will become better understood with reference to the following more detailed description and claims taken in conjunction with the accompanying drawings, in which like elements are identified with like symbols, and in which:

DESCRIPTIVE KEY

Figure 1:
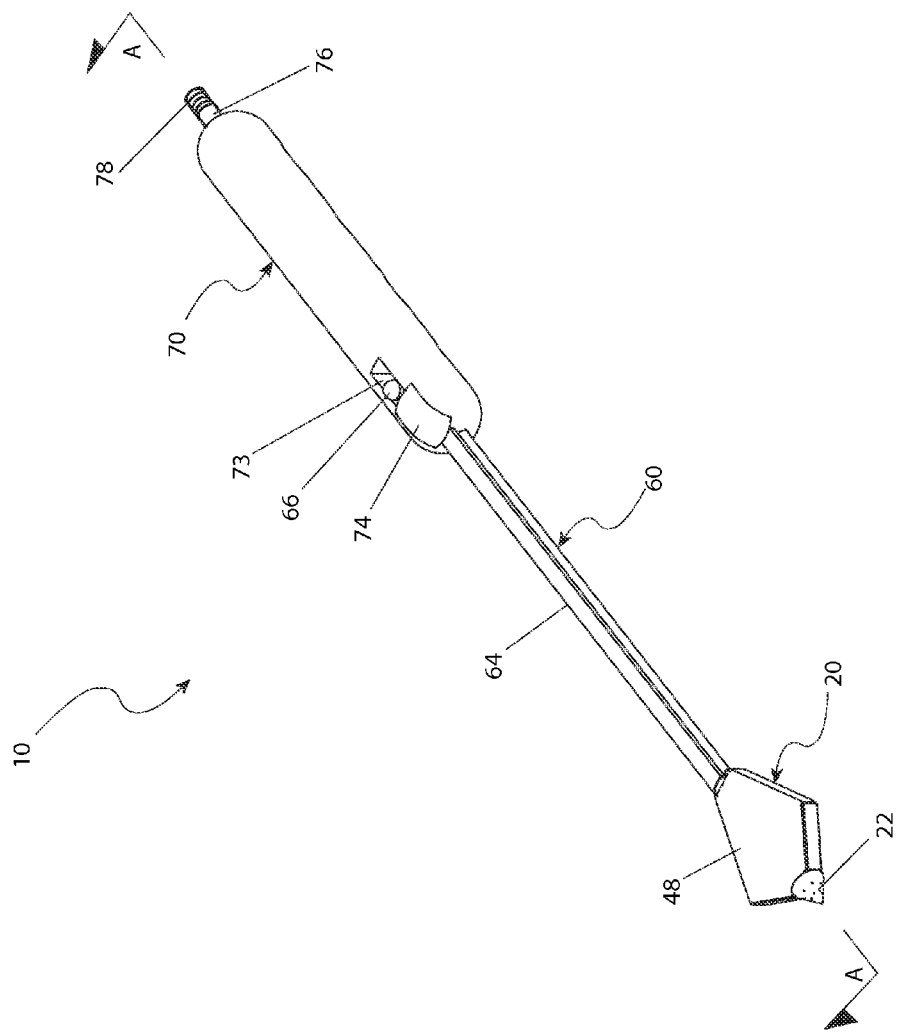
FIG. 1 is a perspective view of a laparoscopic retractor and suction device in accordance with one embodiment of the present invention.

- 10 device
- 20 head
- 22 tip
- 24 suction capillary
- 26 central channel
- 28 stem
- 32 first stationary pivot
- 34 second stationary pivot
- 36 first intermediate pivot
- 38 second intermediate pivot
- 40 sliding collar
- 42 first traversing pivot
- 44 second traversing pivot
- 46 pivot pin
- 48 cover
- 52 first link
- 54 second link
- 56 third link
- 58 fourth link
- 60 shaft
- 62 suction channel
- 64 slide shaft
- 66 knob
- 70 handle
- 72 grip
- 73 cavity
- 74 insert
- 76 vacuum adapter
- 78 barb

DETAILED DESCRIPTION OF THE PREFERRED EMBODIMENT

In accordance with the invention, the best mode is presented in terms of a one or more of the disclosed embodiments, herein depicted within FIGS. 1 through 4. However, the disclosure is not limited to a single described embodiment and a person skilled in the art will appreciate that many other embodiments are possible without deviating from the basic concept of the disclosure and that any such work around will also fall under its scope.

Further, those skilled in the art will recognize that other styles and configurations can be incorporated into the teachings of the present disclosure, and that the example configurations shown and described herein are for the purpose of clarity and disclosure and not by way of limitation.

As used herein, the singular terms "a", "an", and "the" do not denote a limitation of quantity, but rather denote the presence of at least one (1), as well as a plurality of, the referenced items, unless the context clearly indicates otherwise.

As used herein, the terms "first", "second", "third", etc. are used as labels to describe various elements, features, and/or components, and are not intended to impose ordinal, positional, or hierarchical requirements on the referenced items, unless other indicated. For example, such terms may be used to distinguish one (1) element from another element.

As used herein, relative terms such as "front", "rear", "left", "right", "top", "bottom", "below", "above", "upper", "lower", "horizontal", or "vertical" are used to describe a relationship of one (1) element, feature and/or region to another element, feature and/or region as illustrated in the figures.

Referring to FIGS. 1-4, disclosing a laparoscopic retractor and suction device (herein referred to as the "device") 10, where like reference numerals represent similar or like parts. The device 10 provides a means to manipulate internal organs, or portions thereof, and evacuate bodily fluids from an operation field during a laparoscopic surgery.

Figure 2:
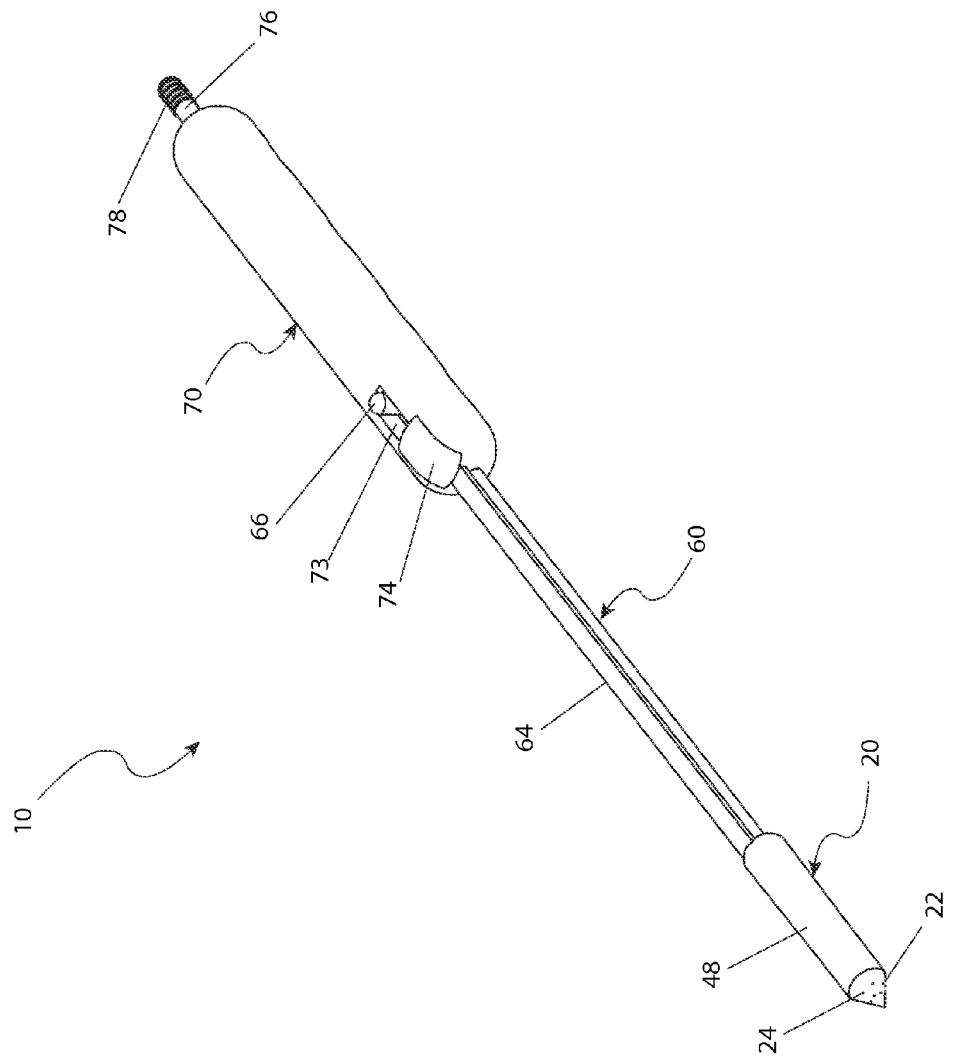
FIG. 2 is a perspective view of the laparoscopic retractor and suction device of FIG. 1 in a collapsed configuration.
Figure 3:
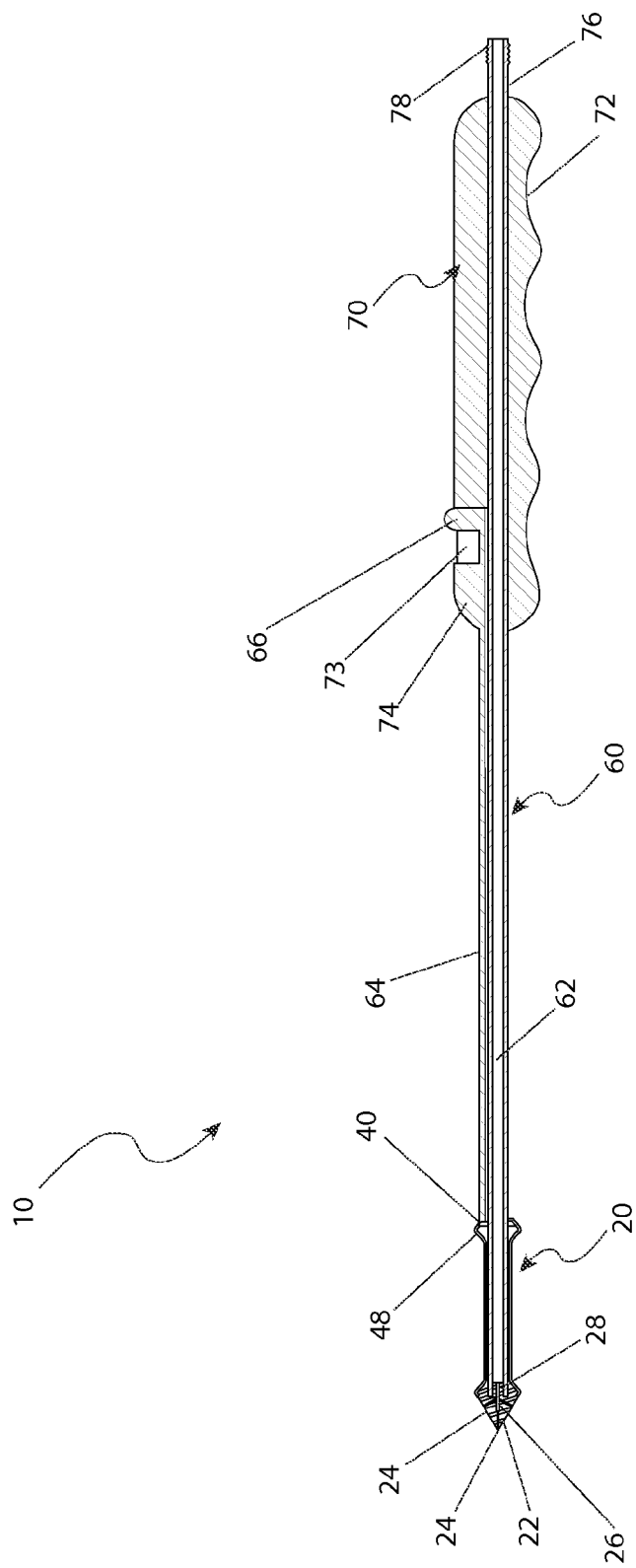
FIG. 3 is a section view along line A-A of FIG. 1 of the laparoscopic retractor and suction; and, FIG. 4 is an enlarged perspective view of a head of the laparoscopic retractor and suction device of FIG. 1 in a deployed configuration.

Referring now to FIG. 1, a perspective view of the device 10 and FIG. 2, a perspective view of the device 10 in a collapsed configuration, according to one (1) embodiment of the present invention, are disclosed. The device 10 includes a shaft 60, a head 20 at a distal end thereof, and a handle 70 at a proximal end thereof. A conical tip 22 is disposed at a distal end of the head 20 and is provided with a stem 28 as seen in FIG. 3.

The tip is preferably composed of a thermoplastic material and formed in an injection molding process. Other materials, such as a surgical quality metal, may be utilized without limiting the scope of the device 10. The tip 22 of the head 20 is attached to the shaft 60, preferably by means of a press fit of the stem 28 into the cylindrical suction channel 62 of the shaft 60. The tip 22 is provided with a plurality of suction capillaries 24 spaced in some pattern and connecting the surface of the tip 22 to an internal central channel 26, as seen in FIG. 3, for the collection and disposal of fluids from the operating field.

The head 20 is provided with a resilient foam cover 48. Other materials, such as nitrile, or silicone, may also be utilized without limiting the scope of the device 10. The cover 48 extends from the proximal end of the tip 22 to the proximal side of a sliding collar 40 and is intended to obviate any contusions or laceration of internal organs encountered by the device 10.

The shaft 60 is preferably a cylindrical tube that provides the mechanical connection of the head 20 to the handle 70 and also provides a fluid conduit through the central suction channel 62 from the tip 22 to the vacuum adapter 76 at the proximal end of the device 10. The shaft 60 is preferably configured to be a thermoplastic tube, however, other materials, such as surgical quality metals, may be utilized without limiting the scope of the device 10. The shaft 60 may be configured as a single tube passing entirely through the handle 70, or alternately may terminate at some point within the handle 70. In either embodiment the suction channel 62 would continue through the handle 70 uninterrupted to the vacuum adapter 76.

The vacuum adapter 76 may be equipped with a hose barb 78 configured as one (1) or more raised ridges intended to more positively retain a vacuum hose (not shown) of a conventional aspiration system, which would convey fluids away from the device 10 in a normal manner.

The handle 70 is a semi-rigid thermoplastic, or rubber-like, cylinder by which a user is able to grasp and manipulate the device 10. The handle 70 is preferably provided with a grip 72 that is configured as a plurality of indentations on a selected side of the handle 70 intended to improve and comfort the user's grasp on the device 10.

Referring now to FIG. 3, a section view along line A-A as seen in FIG. 1 of the device 10, according to one embodiment of the present invention, is disclosed. The internal features of the device 10, although discussed in other areas, are more clearly illustrated in FIG. 3.

Figure 4:
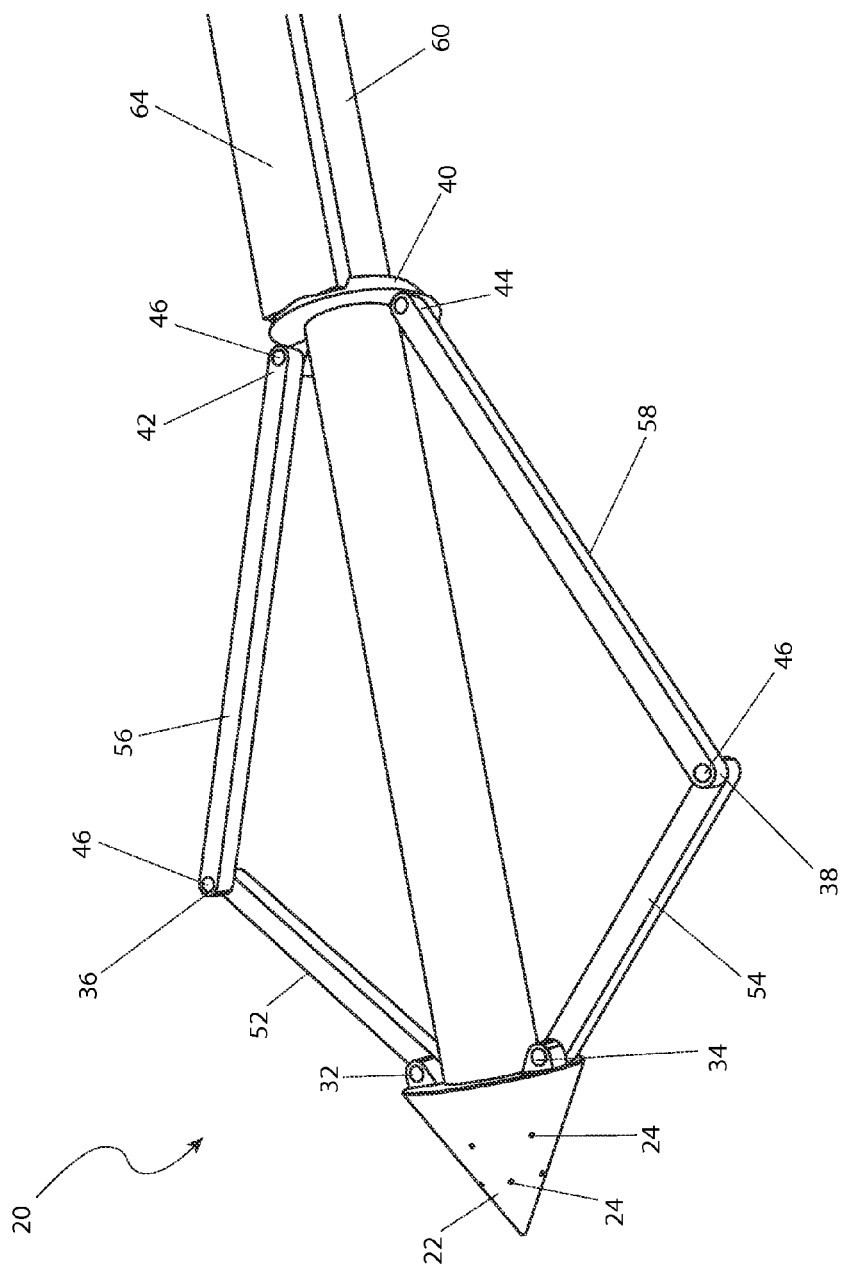

Referring now to FIG. 4, an enlarged perspective view of the head 20 of the device 10, depicted in a deployed configuration without the cover 48, according to one (1)

embodiment of the present invention, is disclosed. The head 20 is configured with an interconnected combination of a first link 52, a second link 54, a third link 56, and a fourth link 58 to flare out a foam cover 48 and is intended to be used to manipulate internal body organs in a surgical field. Disposed at a proximal end of the tip 22, and located off-center thereof near the stem 28, is a first stationary pivot 32 and a second stationary pivot 34. The first stationary pivot 32 and the second stationary pivot 34 are projections of the tip 22 configured to each have an aperture (not shown) for the insertion of a pivot pin 46.

The first link 52 is pivotally attached at a first end to the first stationary pivot 32 by means of a pivot pin 46 inserted through aligned apertures (not shown). The first link 52 is preferably configured to be a small bar of a rigid thermoplastic material having an approximately square cross-section and ends formed on a radius. Other materials, or other details in part formation may be utilized without limiting the scope of the device 10. The second link 54 is configured in an identical fashion as the first link 52 and is pivotally attached at a first end to the second stationary pivot 34 by means of a pivot pin 46 inserted through aligned apertures (not shown).

The pivot pins 46 are preferably composed of a non-reactive metal that could be cold-worked after insertion to form a head or other such obstruction to removal. It is understood that other materials, such as thermoplastics, may also be utilized in the fabrication of the pivot pins 46.

The third link 56 is configured in a similar manner to the first link 52 and is pivotally attached at a first end to a second end of the first link 52 by means of a pivot pin 46 inserted through aligned apertures (not shown) to form a first intermediate pivot 36. A second end of the third link 59 is pivotally attached to a first traversing pivot 42 located on a sliding collar 40 by means of a pivot pin 46 inserted through aligned apertures (not shown). The fourth link 58 is configured identically to the third link 56 and is pivotally attached at a first end to a second end of the second link 54 by means of a pivot pin 46 inserted through aligned apertures (not shown) to form a second intermediate pivot 38. A second end of the fourth link 58 is pivotally attached to a second traversing pivot 44, also located on the sliding collar 40 at a symmetrically opposite location from the first traversing pivot 42, by means of a pivot pin 46 inserted through aligned apertures (not shown).

The sliding collar 40 is preferably configured to be a thermoplastic ring encircling the shaft 60 with the first traversing pivot 42 and the second traversing pivot 44 projecting from a distal side thereof. Attached in a fixed manner to a proximal side of the sliding collar 40 is a slide shaft 64. The slide shaft 64 is the mechanical link between the head 20 and the handle 70 that is used to selectively deploy the head 20 for organ retraction or collapse the head 20 for insertion into and removal from the patient. The slide shaft 64 is preferably a rigid thermoplastic bar having a rectangular cross-section. Other materials, or other shapes may be utilized without limiting the scope of the device 10.

Disposed at a proximal end of the slide shaft 64 is a cylindrical knob 66 having a hemispherical end. At a distal end of the handle 70, on an opposite side from the grip 72 is a cavity 73. The cavity 73 is configured for the disposition of a proximal end of the slide shaft 64 and the attached knob 66 so as to be within a range of motion of the user's thumb. The proximal end of the cavity will limit the retraction of the slide shaft 64 and knob 66.

An insert 74 is fitted into the cavity 73 and retained therein, either by friction, or some other means including one (1) or more threaded fasteners, so as to limit and restrict the forward extension of the slide shaft 64 and knob 66.

Pulling the knob 66 with the thumb toward the vacuum adapter 76 at the proximal end of the handle 70 will move the sliding collar 40 and the attached first traversing pivot 42 and second traversing pivot 44 away from the tip 22. The proximal end of the third link 56 will pivot about the first traversing pivot 42 while moving toward the handle 70 and the distal end of the third link 56 will react at the first intermediate pivot 36 resulting in movement of the first intermediate pivot 36, the distal end of the third link 56, and the proximal end of the first link 52 rearward and towards the shaft 60 as the distal end of the first link 52 pivots about the first stationary pivot 32. Simultaneously, the proximal end of the fourth link 58 will pivot about the second traversing pivot 44 while moving toward the handle 70 and the distal end of the fourth link 58 will react at the second intermediate pivot 38 resulting in movement of the second intermediate pivot 38, the distal end of the fourth link 58, and the proximal end of the second link 54 rearward and towards the shaft 60 as the distal end of the second link 54 pivots about the second stationary pivot 34. With the first intermediate pivot 36 and the second intermediate pivot 38 moved toward the shaft 60 the head 20 is collapsed as shown in FIG. 2. The slide shaft 64 will stop against the proximal end of the cavity 73 prior to the first intermediate pivot 36 and the second intermediate pivot 38 going over-center so that if the button were pushed toward the head 20, those pivots 36, 38 would move away from the shaft 60 to deploy the device 10 as illustrated in FIG. 1. The slight restriction of movement exerted by the insert 74 upon the slide shaft 64 obviates any unintended movement or collapse of the head 20 during normal use.

Those skilled in the art will recognize that other styles and configurations of the disclosed device 10 can be easily incorporated into the teachings of the present disclosure, and only particular configurations have been shown and described for purposes of clarity and disclosure and not by way of limitation of scope.

One embodiment of the disclosed method for utilizing the device 10 includes the following steps: 1). acquiring a model of the device 10; 2). removing the device from the sterile packaging; 3). connecting an existing aspiration line to the vacuum adapter 76; 4). engaging the existing aspiration line fully onto the barbs 78; 5). grasping the handle 70 of the device 10 in the palm of the preferred hand while orienting the head 20 toward the thumb side of the hand and the fingers engaging in the grip 72; 6). inserting the head 20 of the device 10 through a cannula into a patient's abdomen; 7). moving the knob 66 attached to the slide shaft 64 toward the head 20 of the device 10 thus deploying the device 10 for use; and 8). retracting organs as necessary while aspirating fluids as required.

Upon completion of the use of the device 10 it can be removed from the surgery site by sliding the knob 66 along with the attached slide shaft 64 toward the vacuum adapter, thus collapsing the head 20; and removing the head 20 device 10 from the patient's abdomen; and removing the aspiration line.

The foregoing descriptions of specific embodiments have been presented for purposes of illustration and description. They are not intended to be exhaustive or to limit to the precise forms disclosed and many modifications and variations are possible in light of the above teachings. The embodiments were chosen and described in order to best explain principles and practical application to enable others skilled in the art to best utilize the various embodiments with various modifications as are suited to the particular use contemplated.

What is claimed is:

1. A laparoscopic retractor and suction device comprising:
   a shaft comprising a distal end and an opposed proximal end, said shaft defining an internal suction channel extending from said distal end to said proximal end; and,
   a head attached to said distal end of said shaft and in fluid communication with said suction channel, said head being movable from a collapsed configuration to a deployed configuration, further comprising:
      a tip connected to said distal end of said shaft;
      a central channel extending through said tip, said central channel being in fluid communication with said suction channel of said shaft;
      a plurality of suction capillaries extending from an exterior of said tip to said central channel, said plurality of suction capillaries being in fluid communication with said central channel; and,
      a stem connected to said tip;
      wherein said central channel extends through said stem, and;
      wherein said stem is received by said suction channel to connect said head to said shaft and fluidly interconnect said central channel and said suction channel.

2. The device of claim 1, further comprising a handle covering a portion of said shaft about said proximal end of said shaft.

3. The device of claim 2, wherein said proximal end of said shaft extends beyond said handle, and wherein said proximal end of said shaft comprises a vacuum adapter configured to connect to a vacuum hose of an aspiration system.

4. The device of claim 1, wherein said proximal end of said shaft comprises a vacuum adapter comprising a hose barb configured to connectably engage a vacuum hose of an aspiration system and fluidly connect said suction chamber to said vacuum hose.

5. The device of claim 1, wherein said head further comprises:
   a sliding collar movably connected around said shaft;
   a first pair linkages operatively interconnected between said tip and said sliding collar;
   a second pair of linkages operatively interconnected between said tip and said sliding collar, said second pair of linkages being directly opposite said first pair of linkages;
   wherein said first pair of linkages and said second pair of linkages are movable between said collapsed configuration and said deployed configuration in response to movement of said sliding collar.

6. The device of claim 5, wherein said first pair of linkages comprises:
   a first link pivotally connected to said head; and,
   a second link pivotally interconnected to said first link and said sliding collar.

7. The device of claim 5, wherein said second pair of linkages comprises:
   a third link pivotally connected to said head; and,
   a fourth link pivotally interconnected to said second link and said sliding collar.

8. The device of claim 5, wherein said head further comprises an expandable cover disposed over said first pair of linkages and said second pair of linkages, wherein said first pair of linkages and said second pair of linkages move outwardly to expand said cover when in said deployed configuration, and wherein said first pair of linkages and said second pair of linkages move inwardly to retract said cover when in said collapsed configuration.

9. The device of claim 1, further comprising a knob operatively connected to said head for moving said head between said collapsed configuration and said deployed configuration.

10. The device of claim 9, further comprising a slide shaft interconnected between said knob and said head, wherein engagement of said knob linearly moves said slide shaft along said shaft for moving said head between said collapsed configuration and said deployed configuration.

11. The device of claim 10, further comprising a sliding collar movably connected around said shaft, wherein said sliding collar is interconnected between said slide shaft and said head.

12. The device of claim 9, further comprising an insert positioned near said knob to limit movement of said knob.

13. A laparoscopic retractor and suction device comprising:
   a shaft comprising a distal end and an opposed proximal end, said shaft defining an internal suction channel extending from said distal end to said proximal end, and said proximal end of said shaft comprises a vacuum adapter configured to connect to a vacuum hose of an aspiration system and fluidly connect said suction chamber to said vacuum hose;
   a handle covering a portion of said shaft about said proximal end of said shaft, said vacuum adapter extending beyond said handle;
   a head stem receivably connected within said suction channel at said distal end of said shaft;
   a head tip connected to said head stem, said head stem and said head tip defining a central channel extending through said head stem and said head tip and being in fluid communication with said suction channel, said head tip comprising a plurality of suction capillaries extending from an exterior of said head tip to said central channel and being in fluid communication with said central channel;
   a sliding collar movably connected around said shaft;
   a first linkage comprising a first end pivotally connected to said head tip and an opposed second end;
   a second linkage comprising a first end pivotally connected to said head tip and an opposed second end, said first linkage and said second linkage being directly opposite one another relative to said shaft;
   a third linkage comprising a first end pivotally connected to said second end of said first linkage and an opposed second end pivotally connected to said sliding collar;
   a fourth linkage comprising a first end pivotally connected to said second end of said second linkage and an opposed second end pivotally connected to said sliding collar, said third linkage and said fourth linkage being directly opposite one another relative to said shaft;
   a slide shaft comprising a distal end connected to said sliding collar and an opposed proximate end;
   a knob connected to said proximate end of said slide shaft; and,
   an expandable cover disposed over said first, second, third, and fourth linkages;
   wherein linear movement of said knob linearly moves said slide shaft and said sliding collar along said shaft for moving said first and third linkages and said second and fourth linkages between a collapsed configuration and a deployed configuration;

wherein said first and third linkages and said second and fourth linkages move outwardly to expand said cover when in said deployed configuration; and, wherein said first and third linkages and said second and fourth linkages move inwardly to retract said cover when in said collapsed configuration.

14. The device of claim 13, wherein said handle comprises a cavity, and wherein said knob is movably disposed within said cavity.

15. The device of claim 14, wherein said handle further comprises an insert disposed within said cavity to limit linear movement of said knob.

16. The device of claim 13, wherein said vacuum adapter comprises a hose barb configured to connectably engage said vacuum hose.

17. The device of claim 13, wherein said cover comprises a resilient elastic material.

18. The device of claim 13, wherein said head tip comprises a conical shape.

\* \* \* \* \*